US006468956B1

(12) United States Patent
Huish et al.

(10) Patent No.: US 6,468,956 B1
(45) Date of Patent: Oct. 22, 2002

(54) COMPOSITION CONTAINING α-SULFOFATTY ACID ESTER AND HYDROTROPE AND METHODS OF MAKING AND USING THE SAME

(75) Inventors: Paul Danton Huish, Salt Lake City, UT (US); Laurie A. Jensen, Midvale, UT (US); Pule B. Libe, Salt Lake City, UT (US)

(73) Assignee: Huish Detergents, Inc., Salt Lake City, UT (US)

( * ) Notice: Subject to any disclaimer, the term of this patent is extended or adjusted under 35 U.S.C. 154(b) by 0 days.

(21) Appl. No.: 09/578,248

(22) Filed: May 24, 2000

(51) Int. Cl.[7] .................... C11D 17/08; C07C 321/00

(52) U.S. Cl. .................... 510/428; 510/352; 510/429; 134/40; 560/147

(58) Field of Search .................... 510/221, 235, 510/429, 428, 352; 560/147; 134/40

(56) References Cited

U.S. PATENT DOCUMENTS

| | | | | | |
|---|---|---|---|---|---|
| 4,374,056 | A | * | 2/1983 | Watanabe et al. | 252/546 |
| 5,616,781 | A | * | 4/1997 | Sajic et al. | 510/221 |
| 5,637,758 | A | * | 6/1997 | Sajic et al. | 560/147 |
| 5,945,394 | A | * | 8/1999 | Sajic et al. | 510/428 |

* cited by examiner

*Primary Examiner*—Necholus Ogden
(74) *Attorney, Agent, or Firm*—Townsend and Townsend and Crew LLP

(57) ABSTRACT

Compositions containing a α-sulfofatty acid ester and a hydrotrope. The α-sulfofatty acid ester and the hydrotrope reduce the pH drift in the composition and solubilize the α-sulfofatty acid ester in solution. Methods are also disclosed for making such compositions.

20 Claims, No Drawings

COMPOSITION CONTAINING α-SULFOFATTY ACID ESTER AND HYDROTROPE AND METHODS OF MAKING AND USING THE SAME

BACKGROUND OF THE INVENTION

The present invention generally relates to compositions containing α-sulfofatty acid ester and methods for making and using such compositions. More particularly, the present invention relates to compositions containing α-sulfofatty acid ester and hydrotrope, and methods for making and using the same.

Detergents have been used for many years to clean clothing and other materials. Detergents originally contained soap derived from animal fats. More recently, surfactants have been included in detergents to enhance their cleaning performance. Typical surfactants include anionics, nonionics, zwitterionics, ampholytics, cationics and those described in *Surface Active Agents*, Volumes I and II by Schwartz, Perry and Berch (New York, Interscience Publishers), *Nonionic Surfactants*, ed. by M. J. Schick (New York, M. Dekker, 1967), and in McCutcheon's *Emulsifiers & Detergents* (1989 Annual, M. C. Publishing Co.), the disclosures of which are incorporated herein by reference.

Anionic surfactants are a preferred type of surfactant for laundry detergents due to their improved cleaning performance. The cleaning performance of anionic surfactants can be limited, however, by water hardness. Calcium and/or magnesium ions in hard water interfere with some anionic surfactants, such as alkyl olefin sulfonates, alkyl sulfates, linear alkyl sulfonates, and linear alkyl benzene sulfonates. Recently, interest in α-sulfofatty acid esters (also referred to hereafter as "sulfofatty acids") has increased due to the improved cleaning properties of these surfactants in hard water. While α-sulfofatty acid esters and other anionic surfactants have similar detergency in soft water, as water hardness increases α-sulfofatty acid esters exhibit better cleaning performance as compared with other anionic surfactants.

The use of α-sulfofatty acid esters has not been widely accepted, however, due to several disadvantages of such sulfofatty acids. In particular, α-sulfofatty acid esters tend to degrade to form di-salts during their manufacture. While mono-salts of α-sulfofatty acid esters have the desired surface active agent properties, di-salts have several undesirable properties that degrade the performance of the α-sulfofatty acid ester. For example, the Kraft point of a $C_{16}$ methyl ester sulfonate ("MES") di-salt is 65° C., as compared to 17° C. for the mono-salt form of $C_{16}$ MES. (The Kraft point is the temperature at which the solubility of an ionic surfactant becomes equal to its critical micelle concentration; below the Kraft point, surfactants form precipitates instead of micelles.) Thus, the higher the Kraft point, the more di-salt precipitates in the composition. The resulting poor di-salt solubility in cool and even slightly hard water is a disadvantage in most applications. Thus, significant amounts of di-salt in otherwise high quality α-sulfofatty acid ester degrade the performance of that sulfofatty acid. The presence of large amounts of di-salt in α-sulfofatty acid ester, therefore, results in a poorer quality α-sulfofatty acid ester product, characterized by degraded performance and reduced application flexibility.

Di-salts also result from hydrolysis of α-sulfofatty acid ester during storage and in detergent formulations. In particular, mono-salts of α-sulfofatty acid ester hydrolyze in the presence of moisture and alkali-containing detergent components to form di-salts. For example, in formulations where MES is well mixed with high pH components under aqueous conditions, the MES will hydrolyze nearly completely to the di-salt form. High pH components include builders, such as silicates or carbonates, and bases, such as sodium hydroxide (NaOH). This chemical instability discourages the use of α-sulfofatty acid esters in many applications.

A related problem associated with α-sulfofatty acid ester-containing detergent compositions is pH drift. In concentrated solutions, the pH of the solution drifts towards the acidic (lower) range. Such pH drift interferes with other detergent components in the composition. To prevent pH drift, buffering or alkalizing agents are added to detergents. Buffering or alkalizing agents, such as caustic soda (NaOH), cause additional di-salt formation, however, which decreases the performance of the α-sulfofatty acid ester.

α-Sulfofatty acid esters also have limited solubility in concentrated solutions. For example, phase separation occurs in concentrated solutions of $C_{16}$ or $C_{18}$ α-sulfofatty acid esters if the sulfofatty acid ester is not adequately solubilized. To prevent phase separation, a hydrotrope is added to the detergent composition. (A hydrotrope is a compound that is soluble in aqueous solutions and that increases the aqueous solubility of organic compounds.) Common hydrotropes include urea, lower molecular weight alkanols, glycols, and ammonium, potassium or sodium salts of toluene, xylene or cumene or ethyl benzene sulfonates. The latter hydrotropes tend to be more expensive, so less expensive hydrotropes, such as urea ($(NH_2)_2CO$) or urea-alkanol mixtures, are frequently used as cost-effective substitutes. Greater quantities of these hydrotropes are required, however, to achieve the stabilizing effects of the more expensive hydrotropes.

A disadvantage of urea-based hydrotropes, however, is that contaminants in urea release unpleasant odors. In particular, urea often contains ammonium carbamate ($NH_4CO_2NH_2$), which hydrolyzes to release ammonia. If ammonia is released during washing, it can offend the consumer, leading to decreased consumer satisfaction with the product. Urea itself also slowly hydrolyzes to release ammonia. If high levels of urea are present, such hydrolysis tends to increase the pH of the composition. Such high pH values are generally incompatible with some uses of α-sulfofatty acid esters and with other detergent components.

Thus, there is a need for a composition of α-sulfofatty acid ester and hydrotrope that stabilizes the α-sulfofatty acid ester and reduces additional di-salt formation. There is a further need for a hydrotrope that reduces pH drift and/or phase separation by α-sulfofatty acid esters. Surprisingly, the present invention satisfies these needs.

SUMMARY OF THE INVENTION

The present invention provides compositions comprising α-sulfofatty acid ester and hydrotrope. Effective amounts of α-sulfofatty acid ester and hydrotrope are combined to form a stabilized composition. In one embodiment, the hydrotrope solubilizes the α-sulfofatty acid ester in solution and reduces phase separation. In a second embodiment, the effective amounts of the hydrotrope and the α-sulfofatty acid ester reduce pH drift in the composition, thereby reducing di-salt formation. In another embodiment, the hydrotrope reduces di-salt formation by sparing the need for alkalizing agents. In still another embodiment, the hydrotrope provides multiple stabilizing effects.

The composition can optionally include detergent components. In one embodiment, suitable detergent components include, nonionic surfactants, other anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like. In another embodiment, the nonionic surfactant is a polyalkoxylated alkanolamide.

In another embodiment, the hydrotrope is urea. Such urea is preferably substantially free of ammonium carbamate. In still another embodiment, the composition comprises environmentally-friendly, biodegradable components, including α-sulfofatty acid ester, urea, polyalkoxylated alkanolamide, and other biodegradable detergent components.

Methods of making compositions comprising α-sulfofatty acid ester and hydrotrope are also provided. Such methods generally include providing the α-sulfofatty acid ester and the hydrotrope, and mixing these components to form the composition. In another embodiment, detergents components are included in the composition. Such detergent components include, for example, nonionic surfactants, other anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like.

DETAILED DESCRIPTION OF THE INVENTION

The following description provides specific details, such as materials and dimensions, to provide a thorough understanding of the present invention. The skilled artisan, however, will appreciate that the present invention can be practiced without employing these specific details. Indeed, the present invention can be practiced in conjunction with processing, manufacturing or fabricating techniques conventionally used in the detergent industry. Moreover, the processes below describe only steps, rather than a complete process flow, for manufacturing the compositions and detergents containing the compositions of the present invention.

A preferred embodiment is directed to compositions comprising α-sulfofatty acid ester and hydrotrope. The α-sulfofatty acid ester and the hydrotrope are combined to form a stabilized composition according to the present invention.

The α-Sulfofatty Acid Ester

In a preferred embodiment, the composition comprises at least one α-sulfofatty acid ester. Such a sulfofatty acid is typically formed by esterifying a carboxylic acid with an alkanol and then sulfonating the α-position of the resulting ester. The α-sulfofatty acid ester is typically of the following formula (I):

(I)

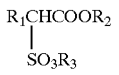

where $R_1$ is a linear or branched alkane, $R_2$ is a linear or branched alkane, and $R_3$ is hydrogen, a halogen, a monovalent or di-valent cation, or an unsubstituted or substituted ammonium cation. $R_1$ can be a $C_4$ to $C_{24}$ alkane, including a $C_{10}$, $C_{12}C_{14}$, $C_{16}$ and/or $C_{18}$ alkane. $R_2$ can be a $C_1$ to $C_8$ alkane, including a methyl group. $R_3$ is typically a monovalent or di-valent cation, such as a cation that forms a water soluble salt with the α-sulfofatty acid ester (e.g., an alkali metal salt such as sodium, potassium or lithium). The α-sulfofatty acid ester of formula (I) can be a methyl ester sulfonate, such as a $C_{16}$ methyl ester sulfonate, a $C_{18}$ methyl ester sulfonate, or a mixture thereof.

More typically, the α-sulfofatty acid ester is a salt, which is generally of the following formula (II):

(II)

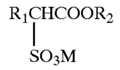

where $R_1$ and $R_2$ are alkanes and M is a monovalent metal. For example, $R_1$ can be an alkane containing 4 to 24 carbon atoms, and is typically a $C_8$, $C_{10}$, $C_{12}$, $C_{14}$, $C_{16}$ and/or $C_{18}$ alkane. $R_2$ is typically an alkane containing 1 to 8 carbon atoms, and more typically a methyl group. M is typically an alkali metal, such as sodium or potassium. The α-sulfofatty acid ester of formula (II) can be a sodium methyl ester sulfonate, such as a sodium $C_8$–$C_{18}$ methyl ester sulfonate.

In one embodiment, the composition comprises at least one α-sulfofatty acid ester. For example, the α-sulfofatty acid ester can be a $C_{10}$, $C_{12}$, $C_{14}$, $C_{16}$ or $C_{18}$ α-sulfofatty acid ester. In another embodiment, the α-sulfofatty acid ester comprises a mixture of sulfofatty acids. For example, the composition can comprise a mixture of α-sulfofatty acid esters, such as $C_{10}$, $C_{12}$, $C_{14}$, $C_{16}$ and $C_{18}$ sulfofatty acids. The proportions of different chain lengths in the mixture are selected according to the properties of the α-sulfofatty acid esters. For example, $C_{16}$ and $C_{18}$ sulfofatty acids (e.g., from tallow and/or palm stearin MES) generally provide better surface active agent properties, but are less soluble in aqueous solutions. $C_{10}$, $C_{12}$ and $C_{14}$ α-sulfofatty acid esters (e.g., from palm kernel oil or coconut oil) are more soluble in water, but have lesser surface active agent properties. Suitable mixtures include $C_8$, $C_{10}$, $C_{12}$ and/or $C_{14}$ α-sulfofatty acid esters with $C_{16}$ and/or $C_{18}$ α-sulfofatty acid esters. For example, about 1 to about 99 weight percent of $C_8$, $C_{10}$, $C_{12}$ and/or $C_{14}$ α-sulfofatty acid ester can be combined with about 99 to about 1 weight percent of $C_{16}$ and/or $C_{18}$ α-sulfofatty acid ester. In another embodiment, the mixture comprises about 1 to about 99 weight percent of a $C_{16}$ or $C_{18}$ α-sulfofatty acid ester and about 99 to about 1 weight percent of a $C_{16}$ or $C_{18}$ α-sulfofatty acid ester. In yet another embodiment, the α-sulfofatty acid ester is a mixture of $C_{18}$ methyl ester sulfonate and a $C_{16}$ methyl ester sulfonate and having a ratio of about 2:1 to about 1:3.

The composition can be enriched for certain α-sulfofatty acid esters, as disclosed in co-pending U.S. patent application Ser. No. 09/574,996 filed May 19, 2000, to provide the desired surfactant properties. The disclosure of that application is incorporated by reference herein. For example, α-sulfofatty acid esters prepared from natural sources, such as palm kernel (stearin) oil, palm kernel (olein) oil, or beef tallow, are enriched for $C_{16}$ and/or $C_{18}$ α-sulfofatty acid esters by addition of the purified or semi-purified α-sulfofatty acid esters to a mixture of α-sulfofatty acid esters. Suitable ratios for enrichment range from greater than 0.5:1, about 1:1, about 1.5:1, to greater than 2:1, and up to about 5:1 to about 6:1, or more, of $C_{16}$–$C_{18}$ to other chain length α-sulfofatty acid esters. An enriched mixture can also comprise about 50 to about 60 weight percent $C_8$–$C_{18}$ α-sulfofatty acid esters and about 40 to about 50 weight percent $C_{16}$ α-sulfofatty acid ester.

Methods of preparing α-sulfofatty acid esters are known to the skilled artisan. (See, e.g., U.S. Pat. Nos. 5,587,500;

5,384,422; 5,382,677; 5,329,030; 4,816,188; and 4,671,900; the disclosures of which are incorporated herein by reference.) α-Sulfofatty acid esters can be prepared from a variety of sources, including beef tallow, palm kernel oil, palm kernel (olein) oil, palm kernel (stearin) oil, coconut oil, soybean oil, canola oil, cohune oil, coco butter, palm oil, white grease, cottonseed oil, corn oil, rape seed oil, soybean oil, yellow grease, mixtures thereof or fractions thereof. Other sources of fatty acids to make α-sulfofatty acid esters include caprylic ($C_8$), capric ($C_{10}$), lauric ($C_{12}$), myristic ($C_{14}$), myristoleic ($C_{14}$), palmitic ($C_{16}$), palmitoleic ($C_{16}$, stearic ($C_{18}$), oleic ($C_{18}$), linoleic ($C_{18}$), linolenic ($C_{18}$), ricinoleic ($C_{18}$), arachidic ($C_{20}$), gadolic ($C_{20}$), behenic ($C_{22}$) and erucic ($C_{22}$) fatty acids. α-Sulfofatty acid esters prepared from one or more of these sources are within the scope of the present invention.

The compositions according to the present invention comprise an effective amount of α-sulfofatty acid ester (i.e., an amount which exhibits the desired cleaning and surfactant properties). In one embodiment, an effective amount is at least about 5 weight percent α-sulfofatty acid ester. In another embodiment, an effective amount is at least about 10 weight percent α-sulfofatty acid ester. In still another embodiment, an effective amount is at least about 25 weight percent, at least about 30 weight percent, or at least about 35 weight percent. These weight percentages are based on the total weight of the composition.

Hydrotrope

The composition is stabilized by an effective amount of the hydrotrope. The hydrotrope provides one or more stabilizing effects to the α-sulfofatty acid ester-containing composition. In one embodiment, the hydrotrope aids in a solubilizing the α-sulfofatty acid ester in an aqueous solution. In another embodiment, the hydrotrope reduces phase separation of the α-sulfofatty acid ester from aqueous components in solution. Effective amounts of hydrotrope to aid in solubilizing α-sulfofatty acid in solution, or in reducing phase separation, are determined by, for example, titrating a solution containing the α-sulfofatty acid ester until the desired quantity of α-sulfofatty acid ester(s) is solubilized.

In another embodiment, effective amounts of the α-sulfofatty acid ester and the hydrotrope stabilize the composition by reducing pH drift towards either more acidic or more basic values. The α-sulfofatty acid ester(s) is combined with an effective amount of the hydrotrope to stabilize the pH of the composition within a desired range, as compared with a non-stabilized composition. In another embodiment, the effective amount of hydrotrope reduces pH drift outside the desired pH range during storage. The effective amount of the hydrotrope is determined, for example, according to the intended shelf life of the composition, so that the pH of the composition remains within the desired pH range during storage.

In another embodiment, the hydrotrope is compatible with the α-sulfofatty acid ester, so that no more than a minor amount of additional di-salt forms in the composition. The hydrotrope can stabilize the composition by reducing pH drift, thereby sparing the requirement for alkalizing agents. As used herein, the term a "minor amount" means no more than about 30 weight percent additional di-salt. More typically, a minor amount is no more than about 15 weight percent additional di-salt, or no more than about 7 weight percent additional di-salt. As will be appreciated by the skilled artisan, the preceding ranges apply to additional di-salt formation and exclude di-salt already present in the α-sulfofatty acid ester as a result of the manufacturing process. The method of George Battaglini et al., *Analytical Methods for Alpha Sulfo Methyl Tallowate*, JOACS, Vol. 63, No. 8 (August, 1986), can be used to determine the amount of di-salt in an α-sulfofatty acid ester sample, and any increase in such a sample as compared with a control sample. The disclosure of this publication is incorporated by reference herein.

In still another embodiment, the hydrotrope provides more than one stabilizing effect. For example, the hydrotrope can aid in solubilizing the α-sulfofatty acid ester and reduce pH drift, thereby reducing di-salt formation.

In a preferred embodiment, the hydrotrope is urea. Typically, α-sulfofatty acid ester is combined with an effective amount of urea to aid in solubilizing the α-sulfofatty acid ester in solution and to reduce pH drift. For example, in some applications an effective amount of α-sulfofatty acid ester ranges from about 5 to about 35 weight percent and an effective amount of urea ranges from about 1 to about 30 weight percent, where the weight percentages are based on the total weight of the composition. In other applications, the effective amount of urea ranges from about 4 to about 20 weight percent. Other examples of effective amounts of α-sulfofatty acid ester and hydrotrope are about 5.4 weight percent α-sulfofatty acid ester (e.g., MES) and about 4 weight percent urea; about 9.45 weight percent α-sulfofatty acid ester and about 7 weight percent urea; about 13.5% weight percent α-sulfofatty acid ester and about 10 weight percent urea; and about 27 weight percent α-sulfofatty acid ester and about 20 weight percent urea. The effective amount of urea is also determined by titrating a solution containing α-sulfofatty acid ester(s) until the composition is stabilized.

In a more preferred embodiment, the urea contains little to no ammonium carbamate. For example, such urea preferably contains less than about 0.1 weight percent ammonium carbamate.

The composition can optionally further include a secondary hydrotrope. Such a secondary hydrotrope can be a Kraft point reducer that helps prevent precipitation of the α-sulfofatty acid ester at lower temperatures. As will be appreciated by the skilled artisan, precipitation is generally indicated by the presence of white turbidity in the solution. Examples of suitable Kraft point reducers include, but are not limited to, pyrrolidones, such as, for example, N-octyl pyrrolidone (SURFADONE®, International Specialty Products, UK), the pyridone salts disclosed in U.S. Pat. No. 4,367,169, the disclosure of which is incorporated by reference herein, and the like. In one embodiment, the composition comprises about 1 to about 5 percent by weight of the Kraft point reducer, although greater and lesser amounts can be used.

OTHER COMPONENTS

In another preferred embodiment, the composition includes other detergent components, such as nonionic surfactants, other (secondary) anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like.

Suitable nonionic surfactants include polyalkoxylated alkanolamides, which are generally of the following formula (III):

(III)

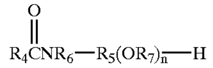

where $R_4$ is an alkane or hydroalkane, $R_5$ and $R_7$ are alkanes and n is a positive integer. $R_4$ is typically an alkane containing 6 to 22 carbon atoms. $R_5$ is typically an alkane containing 1–8 carbon atoms. $R_7$ is typically an alkane containing 1 to 4 carbon atoms, and more typically an ethyl group. The degree of polyalkoxylation (the molar ratio of the oxyalkyl groups per mole of alkanolamide) typically ranges from about 1 to about 100, or from about 3 to about 8, or about 5 to about 6. $R_6$ can be hydrogen, an alkane, a hydroalkane group or a polyalkoxylated alkane. The polyalkoxylated alkanolamide is typically a polyalkoxylated mono- or di-alkanolamide, such as a $C_{16}$ and/or $C_{18}$ ethoxylated monoalkanolamide, or an ethoxylated monoalkanolamide prepared from palm kernel oil or coconut oil.

Methods of manufacturing polyalkoxylated alkanolamides are known to the skilled artisan. (See, e.g., U.S. Pat. Nos. 6,034,257 and 6,034,257, the disclosures of which are incorporated by reference herein.) Sources of fatty acids for the preparation of alkanolamides include beef tallow, palm kernel (stearin or olein) oil, coconut oil, soybean oil, canola oil, cohune oil, palm oil, white grease, cottonseed oil, mixtures thereof and fractions thereof. Other sources include caprylic ($C_8$), capric ($C_{10}$), lauric ($C_{12}$), myristic ($C_{14}$), myristoleic ($C_{14}$), palmitic ($C_{16}$), palmitoleic ($C_{16}$), stearic ($C_{18}$,), oleic ($C_{18}$), linoleic ($C_{18}$), linolenic ($C_{18}$), ricinoleic ($C_{18}$), arachidic ($C_{20}$), gadolic ($C_{20}$), behenic ($C_{22}$) and erucic ($C_{22}$) fatty acids. Polyalkoxylated alkanolamides from one or more of these sources are within the scope of the present invention.

The composition typically comprises an effective amount of polyalkoxylated alkanolamide (e.g., an amount which exhibits the desired surfactant properties). In some applications, the composition contains about 1 to about 10 weight percent of a polyalkoxylated alkanolamide. Typically, the composition comprises at least about one weight percent of polyalkoxylated alkanolamide.

Other suitable nonionic surfactants include those containing an organic hydrophobic group and a hydrophilic group that is a reaction product of a solubilizing group (such as a carboxylate, hydroxyl, amido or amino group) with an alkylating agent, such as ethylene oxide, propylene oxide, or a polyhydration product thereof (such as polyethylene glycol). Such nonionic surfactants include, for example, polyoxyalkylene alkyl ethers, polyoxyalkylene alkylphenyl ethers, polyoxyalkylene sorbitan fatty acid esters, polyoxyalkylene sorbitol fatty acid esters, polyalkylene glycol fatty acid esters, alkyl polyalkylene glycol fatty acid esters, polyoxyethylene polyoxypropylene alkyl ethers, polyoxyalkylene castor oils, polyoxyalkylene alkylamines, glycerol fatty acid esters, alkylglucosamides, alkylglucosides, and alkylamine oxides. Other suitable surfactants include those disclosed in U.S. Pat. Nos. 5,945,394 and 6,046,149, the disclosures of which are incorporated herein by reference. In another embodiment, the composition is substantially free of nonylphenol nonionic surfactants. In this context, the term "substantially free" means less than about one weight percent.

Polymer dispersants, such as polymers and α-polymers of acrylic acid, methacrylic acid, maleic acid, fumaric acid, itaconic acid, and water-soluble salts thereof, such as alkali metal, ammonium, or substituted ammonium salts, can optionally be included in the composition. Suitable polymer dispersants further include those sold under the trade names ACUSOL® 445 (polyacrylic acid), ACUSOL® 445N (polyacrylic acid sodium salt), ACUSOL® 460N (a maleic acid/olefin copolymer sodium salt), and ACUSOL® 820 (acrylic copolymer), sold by Rohm and Haas Company.

In another embodiment, a secondary anionic surfactant is included in the composition. Suitable secondary anionic surfactants includes those surfactants that contain a long chain hydrocarbon hydrophobic group in their molecular structure and a hydrophilic group, i.e., water solubilizing group including salts such as carboxylate, sulfonate, sulfate or phosphate groups. Suitable anionic surfactant salts include sodium, potassium, calcium, magnesium, barium, iron, ammonium and amine salts. Other suitable secondary anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts of alkyl benzene sulfonates having between 8 and 22 carbon atoms in the alkyl group, alkyl ether sulfates having between 8 and 22 carbon atoms in the alkyl group. Other anionic surfactants include polyethoxylated alcohol sulfates, such as those sold under the trade name CALFOAM® 303 (Pilot Chemical Company, California). Examples of other anionic surfactants are disclosed in U.S. Pat. No. 3,976,586, the disclosure of which is incorporated by reference herein. In another embodiment, the composition is substantially free of additional (secondary) anionic surfactants.

Suitable zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds, such as those disclosed in U.S. Pat. No. 3,929,678, which is incorporated by reference herein.

Other suitable components include organic or inorganic detergency builders. Examples of water-soluble inorganic builders that can be used, either alone or in combination with themselves or with organic alkaline sequestrant builder salts, are glycine, alkyl and alkenyl succinates, alkali metal carbonates, alkali metal bicarbonates, phosphates, polyphosphates and silicates. Specific examples of such salts are sodium tripolyphosphate, sodium carbonate, potassium carbonate, sodium bicarbonate, potassium bicarbonate, sodium pyrophosphate and potassium pyrophosphate. Examples of organic builder salts that can be used alone, or in combination with each other, or with the preceding inorganic alkaline builder salts, are alkali metal polycarboxylates, water-soluble citrates such as sodium and potassium citrate, sodium and potassium tartrate, sodium and potassium ethylenediaminetetracetate, sodium and potassium N(2-hydroxyethyl)-nitrilo triacetates, sodium and potassium N-(2-hydroxyethyl)-nitrilo diacetates, sodium and potassium oxydisuccinates, and sodium and potassium tartrate mono- and di-succinates, such as those described in U.S. Pat. No. 4,663,071, the disclosure of which is incorporated herein by reference.

Suitable biocidal agents include triclosan (5-chloro-2(2, 4-dichloro -phenoxy)phenol)), and the like. Suitable optical brighteners include stilbenes such as TINOPAL® AMS, distyrylbiphenyl derivatives such as TINOPAL® CBS-X, stilbene/naphthotriazole blends such as TINOPAL® RA-16, all sold by Ciba Geigy, oxazole derivatives, and coumarin brighteners.

Suitable enzymes include those known in the art, such as amylolytic, proteolytic, cellulolytic or lipolytic type, and those listed in U.S. Pat. No. 5,958,864, the disclosure of which is incorporated herein by reference. One preferred protease, sold under the trade name SAVINASE® by Novo Nordisk Industries A/S, is a subtillase from Bacillus lentus. Other suitable enzymes include proteases, amylases, lipases and cellulases, such as ALCALASE® (bacterial protease), EVERLASE® (protein-engineered variant of SAVINASE®), ESPERASET® (bacterial protease), LIPOLASE® (fungal lipase), LIPOLASE ULTRA (Protein-engineered variant of LIPOLASE), LIPOPRIME™ (protein-engineered variant of LIPOLASE), TERMAMYL® (bacterial amylase), BAN (Bacterial Amylase Novo), CELLUZYME® (fungal enzyme), and CAREZYME® (monocomponent cellulase), sold by Novo Nordisk Industries A/S.

Suitable foam stabilizing agents include a polyalkoxylated alkanolamide, amide, amine oxide, betaine, sultaine, $C_8$–$C_{18}$ fatty alcohols, and those disclosed in U.S. Pat. No. 5,616,781, the disclosure of which is incorporated by reference herein. Foam stabilizing agents are used, for example, in amounts of about 1 to about 20, typically about 3 to about 5 percent by weight. The composition can further include an auxiliary foam stabilizing surfactant, such as a fatty acid amide surfactant. Suitable fatty acid amides are $C_8$–$C_{20}$ alkanol amides, monoethanolamides, diethanolamides, and isopropanolamides. Suitable liquid carriers include water, a mixture of water and a $C_1$–$C_4$ monohydric alcohol (e.g., ethanol, propanol, isopropanol, butanol, and mixtures thereof), and the like. In one embodiment, a liquid carrier comprises from about 90% to about 25% by weight, typically about 80% to about 50% by weight, more typically about 70% to about 60% by weight of the composition. Other suitable components include diluents, dyes and perfumes. Diluents can be inorganic salts, such as sodium and potassium sulfate, ammonium chloride, sodium and potassium chloride, sodium bicarbonate, and the like. Such diluents are typically present at levels of from about 1% to about 10%, preferably from about 2% to about 5% by weight.

Compositions according to the present invention are formed by any suitable method known to the skilled artisan. Typically, effective amounts of α-sulfofatty acid ester and hydrotrope are combined to form the composition. In one embodiment, the urea is solubilized in a liquid carrier (e.g., water) prior to the addition of the α-sulfofatty acid ester. Other suitable methods include those described in *Perry's Chemical Engineers' Handbook* ($6^{th}$ Ed.), chapter 19 (1984), the disclosure of which is incorporated by reference herein. In another embodiment, effective amounts of α-sulfofatty acid ester, the hydrotrope, and other detergent components are combined, according to the desired properties of the final composition. For example, the α-sulfofatty acid ester and hydrotrope are combined in a mixer, other detergent components are added, then the components are mixed to form a composition, according to the present invention.

Other embodiments of the present invention are exemplified in the following examples, which illustrate embodiments according to the present invention, although the invention is not intended to be limited by or to these examples.

EXAMPLE 1

A base for a laundry detergent is formulated by combining the following components:

| | |
|---|---|
| α-sulfofatty acid ester | 5–35 weight percent |
| urea | 1–30 weight percent |
| Other components and water | Balance |

EXAMPLE 2

A liquid laundry detergent is formulated as follows:

| | |
|---|---|
| α-sulfofatty acid ester (palm kernel oil α-sulfofatty acid ester, 50–60%) ($C_{16}$ α-sulfofatty acid ester, 40–50%) | 5–35 weight percent |
| Urea | 1–30 weight percent |
| Polyethoxylated monoalkanolamide ($C_{16}$–$C_{18}$ with a degree of ethoxylation of about 4–6) | 1–10 weight percent |
| Other detergent components | Balance |

EXAMPLE 3

A base for a biodegradable laundry detergent is formulated as follows:

| | |
|---|---|
| α-sulfofatty acid ester (50% palm kernel oil α-sulfofatty acid ester plus 50% $C_{16}$ α-sulfofatty acid ester) | 25–30 weight percent |
| Urea | 10 weight percent |
| Polyethoxylated monoalkanolamide ($C_{16-18}$ with a degree of ethoxylation of | 10 weight percent |
| Liquid carrier | Balance |

Other biodegradable components are added to the base, according to the desired properties of the final composition.

EXAMPLE 4

The stability of liquid laundry detergents containing α-sulfofatty acid esters was tested. Compositions A–F were prepared as follows, where the amounts of each component are listed as weight percentages:

TABLE 1

| | Compositions | | | | | |
|---|---|---|---|---|---|---|
| Components | A | B | C | D | E | F |
| Urea | 4.0 | 7.0 | 10.0 | 0 | 0 | 0 |
| $C_{16}$ alpha sulfofatty acids | 2.4 | 4.2 | 6.0 | 2.4 | 4.2 | 6.0 |
| $C_{8-18}$ alpha sulfofatty acid | 3.0 | 5.3 | 7.5 | 3.0 | 5.3 | 7.5 |
| Polyalkoxylated amide (5.5 moles EO) | 2.0 | 3.5 | 5.0 | 2.0 | 3.5 | 5.0 |
| TEA | 0.8 | 1.4 | 2.0 | 0.8 | 1.4 | 2.0 |
| Preservatives | 0.3 | 0.2 | 0.1 | 0.3 | 0.2 | 0.1 |
| Brightener | 0.2 | 0.2 | 0.4 | 0.2 | 0.2 | 0.4 |

TABLE 1-continued

| Components | Compositions A | B | C | D | E | F |
|---|---|---|---|---|---|---|
| Sodium Gluconate | 0.1 | 0.1 | 0.1 | 0.1 | 0.1 | 0.1 |
| Fragrance | 0.2 | 0.2 | 0.2 | 0.2 | 0.2 | 0.2 |
| Enzymes | 0 | 0 | 0.7 | 0 | 0 | 0.7 |
| Water | Balance | Balance | Balance | Balance | Balance | Balance |
| Total | 100.0 | 100.0 | 100.0 | 100.0 | 100.0 | 100.0 |

EXAMPLE 5

The pH of compositions A–F was measured at 0, 6 and 9 days. The results are shown in the following Table 2:

TABLE 2

| Elapsed time, days | pH Profile A | B | C | D | E | F |
|---|---|---|---|---|---|---|
| 0 | 9.5 | 9.5 | 9.5 | 9.5 | 9.5 | 9.5 |
| 6 | 9.5 | 9.6 | 9.6 | 9.2 | 9.1 | 9.0 |
| 9 | 9.5 | 9.5 | 9.6 | 9.3 | 9.3 | 9.2 |

As shown in Table 2, stabilized compositions A–C (containing α-sulfofatty acid ester and a hydrotrope (urea)) exhibit reduced pH drift, while unstabilized compositions D–F (without hydrotrope) exhibit pH drift towards the acidic range after 9 days. As will be appreciated by the skilled artisan, the pH of the composition will continue to be more acidic over longer time periods.

EXAMPLE 6

The phase stability of compositions A–F was measured by visually observing compositions A–F for a period of 9 days. Composition instability was indicated by the formation of a precipitate. Referring to Table 3, the results of the stability testing are as follows:

TABLE 3

| Elapsed time, days | Phase Stability A | B | C | D | E | F |
|---|---|---|---|---|---|---|
| 0 | Stable | Stable | Stable | Not stable | Not stable | Not stable |
| 6 | Stable | Stable | Stable | Not stable | Not stable | Not stable |
| 9 | Stable | Stable | Stable | Not stable | Not stable | Not stable |

EXAMPLE 7

A heavy duty liquid laundry detergent is formulated as follows:

| | |
|---|---|
| α-sulfofatty acid ester (sodium methyl ester sulfonate derived from palm kernel oil) | 25–35 weight percent |
| Urea | 5–10 weight percent |
| Polyethoxylated monoalkanolamide ($C_{16-18}$ with a degree of ethoxylation of about 4–6) | 1–5 weight percent |

-continued

| | |
|---|---|
| Protease enzyme | 0.9 weight percent |
| Amylase enzyme | 0.2 weight percent |
| Perfume | 0.5 weight percent |
| Inorganic Salt | 2.1 weight percent |
| Water | Balance |

Having thus described in detail the preferred embodiments of the present invention, it is to be understood that the invention defined by the appended claims is not to be limited by particular details set forth in the above description, as many apparent variations thereof are possible without departing from the spirit or scope thereof.

What is claimed is:

1. A liquid composition of a stabilized composition of an effective amount of α-sulfofatty acid ester and urea in an amount effective to solubilize the α-sulfofatty acid ester in solution and to reduce pH drift of the composition; and consisting essentially of additional detergent components selected from the group consisting of nonionic surfactant, secondary anionic surfactant, cationic surfactant, zwitterionic surfactant, secondary hydrotrope, polymer dispersant, builder, oxidizing agent, biocidal agent, foam regulator, activator, catalyst, thickener, fragrance, soil suspending agent, brightener, enzyme, UV protector, salt, water and inert ingredient;

wherein no more than a minor amount of additional amount of disalt formation occurs.

2. The composition of claim 1, wherein the nonionic surfactant is a polyalkoxylated alkanolamide.

3. The composition of claim 2, wherein the polyalkoxylated alkanolamide is a $C_{16}$ ethoxylated monoalkanolamide, a $C_{18}$ ethoxylated monoalkanolamide or mixture thereof.

4. The composition of claim 1, wherein the urea is substantially fee of ammonium carbamate.

5. The composition of claim 1, wherein the α-sulfofatty acid ester is a methyl ester sulfonate.

6. The composition of claim 1, wherein the α-sulfofatty acid ester is a mixture of methyl ester sulfonates.

7. The composition of claim 6, wherein the α-sulfofatty acid ester is enriched for $C_{16}$ α-sulfofatty acid ester.

8. The composition of claim 1, wherein the secondary hydrotrope is a Kraft point reducer.

9. A liquid detergent composition, consisting essentially of:

a stabilized composition of an effective amount of α-sulfofatty acid ester and urea in an amount effective to solubilize the α-sulfofatty acid ester and reduce pH drift of the composition, the urea being substantially free of ammonium carbamate;

polyalkoxylated alkanolamide; and optionally, additional detergent components;

wherein no more than a minor amount of additional di-salt forms in the composition.

10. The composition of claim 9, wherein the additional detergent component is a Kraft point reducer.

11. The composition of claim 9, wherein the α-sulfofatty acid ester is prepared from beef tallow, palm kernel oil, coconut oil, soybean oil, canola oil, cohune oil, coco butter, palm oil, white grease, cottonseed oil, corn oil, rape seed oil, yellow grease, mixtures thereof, or fractions thereof.

12. The composition of claim 9, wherein the α-sulfofatty acid ester is a methyl ester sulfonate.

13. The composition of claim 9, wherein the additional detergent component is nonionic surfactant, other anionic surfactant, cationic surfactant, zwitterionic surfactant, polymer dispersant, builder, oxidizing agent, biocidal agent, foam regulator, activators, catalyst, thickener, fragrance, soil suspending agent, brightener, enzyme, UV protector, salt, water, or inert ingredient.

14. The composition of claim 9, wherein the α-sulfofatty acid ester is a $C_{16}$-enriched methyl ester sulfonate.

15. A liquid detergent composition of a stabilized composition of:

at least about 25 weight percent of methyl ester sulfonate;

at least about 10 weight percent of urea; and consisting essentially of polyalkoxylated alkanolamide and additional detergent components selected from the group consisting of nonionic surfactant, secondary anionic surfactant, cationic surfactant, zwitterionic surfactant, secondary hydrotrope, polymer dispersant, builder, oxidizing agent, biocidal agent, foam regulator, activator, catalyst, thickener, fragrance, soil suspending agent, brightener, enzyme, UV protectors, salt, water and inert ingredient;

whereby the methyl ester sulfonate is protected from more than a minor amount of additional di-salt formation.

16. A method for making a stabilized detergent composition, comprising:

providing α-sulfofatty acid ester;

combining the α-sulfofatty acid ester with an effective amount of urea to solubilize the α-sulfofatty acid ester in solution and to stabilize the pH of the composition to form a pH stabilized composition;

and mixing the pH stabilized composition with other detergent components;

whereby no more than a minor the amount of additional di-salt forms in the composition.

17. The method of claim 16, wherein the α-sulfofatty acid ester is a methyl ester sulfonate.

18. The method of claim 17, further comprising:

enriching the $C_{16}$ content of the methyl ester sulfonate.

19. The method of claim 16, further comprising:

providing a polyalkoxylated alkanolamide; and combining the polyalkoxylated alkanolamide with the α-sulfofatty acid ester.

20. The method of claim 16, wherein the urea is substantially free of ammonium carbamate.

* * * * *